United States Patent
Bersier et al.

(10) Patent No.: US 11,001,552 B2
(45) Date of Patent: May 11, 2021

(54) METHOD FOR PREPARATION OF 5-FLUORO-2-METHYL-3-NITROBENZOIC ACID AND ITS METHYL ESTER

(71) Applicant: LONZA LTD, Visp (CH)

(72) Inventors: Michael Bersier, Ausserberg (CH); Anna Kulesza, Ausserberg (CH); Paul Hanselmann, Brig-Glis (CH); Christof Aellig, Spiez (CH); Sarah Filliger, Naters (CH)

(73) Assignee: LONZA LTD, Visp (CH)

( * ) Notice: Subject to any disclaimer, the term of this patent is extended or adjusted under 35 U.S.C. 154(b) by 12 days.

(21) Appl. No.: 16/620,001

(22) PCT Filed: Jul. 16, 2018

(86) PCT No.: PCT/EP2018/069192
§ 371 (c)(1),
(2) Date: Dec. 6, 2019

(87) PCT Pub. No.: WO2019/016110
PCT Pub. Date: Jan. 24, 2019

(65) Prior Publication Data
US 2021/0078933 A1    Mar. 18, 2021

Related U.S. Application Data

(60) Provisional application No. 62/533,712, filed on Jul. 18, 2017.

(30) Foreign Application Priority Data

Jul. 18, 2017   (EP) ..................................... 17181783

(51) Int. Cl.
*C07C 201/08*     (2006.01)
*C07C 205/58*     (2006.01)

(52) U.S. Cl.
CPC .......... *C07C 201/08* (2013.01); *C07C 205/58* (2013.01)

(58) Field of Classification Search
CPC .................. C07C 201/08; C07C 205/58
See application file for complete search history.

(56) References Cited

U.S. PATENT DOCUMENTS

| 2,934,571 | A | 4/1960 | Bonetti |
| 3,397,229 | A * | 8/1968 | Welch .................. C07C 205/57 562/438 |
| 2005/0272823 | A1 | 12/2005 | Rehwinkel et al. |
| 2017/0313676 | A1 * | 11/2017 | Ge .......................... A61P 35/02 |

FOREIGN PATENT DOCUMENTS

| CN | 101314589 A | 12/2008 |
| CN | 101357891 A | 2/2009 |
| WO | 2009112832 A1 | 9/2009 |
| WO | 2014/086894 A1 | 6/2014 |
| WO | 2015/101670 A2 | 7/2015 |
| WO | 2015180613 A1 | 12/2015 |
| WO | 2018/137639 A1 | 8/2018 |

OTHER PUBLICATIONS

Office Action dated Jun. 9, 2020 from corresponding Japanese Patent Application No. 2019-568102, 5 pages including English translation.
Office Action dated Sep. 16, 2020 from corresponding Chinese Patent Application No. 201880047848.6, 14 pages including English translation.
Gillmore et al., "Multkilogram Scale-Up of a Reductive Alkylation Route to a Novel PARP Inhibitor", Organic Process Research and Development, vol. 16, No. 12, (2012), pp. 1897-1904.
International Preliminary Examination Report (IPER) issued by International Preliminary Examination Authority in corresponding International Application No. PCT/EP2018/069192 dated Jun. 28, 2019, pp. 1-9 (also referred to as Chapter II International Preliminary Report on Patentability).
International Search Report and Written Opinion issued in corresponding International Application No. PCT/EP2018/069192 dated Sep. 4, 2018, pp. 1-12.

* cited by examiner

*Primary Examiner* — Jafar F Parsa
(74) *Attorney, Agent, or Firm* — MH2 Technology Law Group, LLP

(57) ABSTRACT

The invention discloses a method for preparation of 5-fluoro-2-methyl-3-nitrobenzoic acid and its methyl ester by conversion of 5-fluoro-2-methylbenzoic acid with fuming nitric acid and oleum and subsequent conversion with methanol.

14 Claims, No Drawings

METHOD FOR PREPARATION OF 5-FLUORO-2-METHYL-3-NITROBENZOIC ACID AND ITS METHYL ESTER

CROSS-REFERENCE TO RELATED APPLICATIONS

This application is a U.S. National Stage application of PCT/EP2018/069192 filed 16 Jul. 2018, which claims priority to U.S. Provisional Patent Application No. 62/533,712 filed 18 Jul. 2017, and European Patent Application No. 17181783.6 filed 18 Jul. 2017, the entire disclosures of which are hereby incorporated by reference in their entireties.

The invention discloses a method for preparation of 5-fluoro-2-methyl-3-nitrobenzoic acid and its methyl ester by conversion of 5-fluoro-2-methylbenzoic acid with fuming nitric acid and oleum and subsequent conversion with methanol.

BACKGROUND OF THE INVENTION

Rucaparib, also known as CO-338, is an inhibitor of poly ADP-ribose polymerase (PARP) inhibitor.

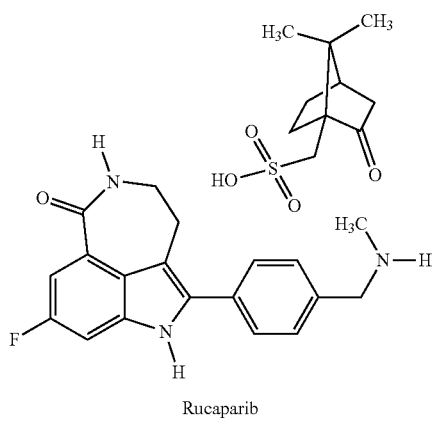

Rucaparib

Rucaparib is being developed for the treatment of patients with cancers pre-disposed to PARP inhibitor sensitivity.

Gillmore et al., Org. Process Res. Dev., 2012, 16, 1897-1904, discloses the use of methyl-5-fluoro-2-methyl-3-nitro benzoate for the preparation of Rucaparib. 52% yield of a brown solid is reported for the two steps conversion of 5-fluoro-2-methylbenzoic acid to 5-fluoro-2-methyl-3-nitrobenzoic acid methyl ester by nitration with concentrated sulfuric acid and concentrated nitric acid followed by subsequent esterification.

WO 2009/112832 A1 discloses in Example 5 the nitration of 5-fluoro-2-methylbenzoic acid with fuming $HNO_3$ and $H_2SO_4$ conc. 5-Fluoro-2-methyl-3-nitrobenzoic acid is obtained as a yellow solid.

US2005/0272823 A1 discloses in paragraph [495] the nitration of 5-fluoro-2-methylbenzoic acid with a mixture fuming nitric acid and concentrated sulfuric acid. The yield is 45.1% of a mixture of various regioisomers and by-products.

There was a need for a process that has higher yield and higher purity.

It was found that the use of oleum and fuming nitric acid increases the yield. In addition a colorless product is obtained. Also the content of the undesired dinitro derivative is low.

The following abbreviations are used, if not otherwise stated:
eq eqivalent
TFA trifluoro acetic acid
wt % percent by weight

SUMMARY OF THE INVENTION

Subject of the invention is a method for the preparation of compound of formula (2)

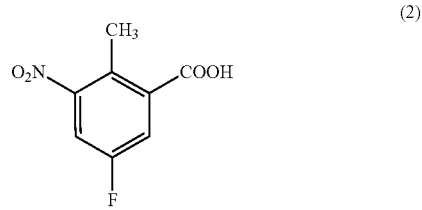

comprising a step STEP1, STEP1 comprises a reaction REAC1, in REAC1 compound of formula (1)

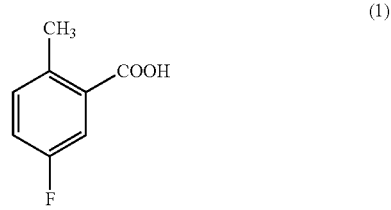

is converted to compound of formula (2) by the action of a mixture MIX of concentrated sulphuric acid, oleum and fuming nitric acid.

DETAILED DESCRIPTION OF THE INVENTION

Preferably, the concentrated sulfuric acid is conventional concentrated sulfuric acid; more preferably the concentrated sulfuric acid has a content of from 94 to 100 wt % of $H_2SO_4$; even more preferably of from 95 to 100 wt % of $H_2SO_4$; especially of from 96 to 100 wt % of $H_2SO_4$;
the wt % based on the weight of the concentrated sulfuric acid.
Preferably, the oleum is conventional oleum;
more preferably the oleum contains 50 to 70 wt % of $SO_3$;
even more preferably the oleum contains 60 to 70 wt % of $SO_3$.
Preferably, the fuming nitric acid is conventional fuming nitric acid;
preferably the fuming nitric acid has a content of from 95 to 100 wt % of $HNO_3$;
more preferably of from 98 to 100 wt % of $HNO_3$.
Preferably, MIX contains
concentrated sulphuric acid in an amount of 4 to 12 times of molar equivalents of $H_2SO_4$ relative to compound of formula (1),
oleum in an amount of 1 to 4 molar times of equivalents of $H_2SO_4$ relative to compound of formula (1),
fuming nitric acid in an amount of 1 to 2 times of molar equivalents of $HNO_3$ relative to compound of formula (1);

more preferably, MIX contains
concentrated sulphuric acid in an amount of 4 to 6 times of molar equivalents of $H_2SO_4$ relative to compound of formula (1),
oleum in an amount of 2 to 4 molar times of equivalents of $H_2SO_4$ relative to compound of formula (1),
fuming nitric acid in an amount of 1.5 to 2 times of molar equivalents of $HNO_3$ relative to compound of formula (1);
preferably the amounts of concentrated sulfuric acid, oleum and fuming nitric acid in MIX add up to 95 to 100 wt %, more preferably to 98 to 100 wt %, the wt % being based on the total weight of MIX; even more preferably MIX consists of concentrated sulfuric acid, oleum and fuming nitric acid.

REAC1 can be done batch wise or in a continuous way. Preferably, the reaction temperature TEMP1 of REAC1 is from −10 to 30° C., more preferably from −5 to 25° C. Preferably, the reaction time TIME1 of REAC1 is from 1 sec to 2 h, more preferably from 10 min to 1.5 h.
When REAC1 is done batch wise, then
preferably, the reaction temperature TEMP1 of REAC1 is from −10 to 20° C., more preferably from −5 to 5° C.
When REAC1 is done in a continuous way, then
preferably, the reaction temperature TEMP1 of REAC1 is from 10 to 30° C., more preferably from 15 to 25° C.
When REAC1 is done batch wise, then
preferably, the reaction time TIME1 of REAC1 is from 30 min to 2 h, more preferably from 45 min to 1.5 h.
When REAC1 is done in a continuous way, then
preferably, the reaction time TIME1 of REAC1 is from 1 sec to 30 min, more preferably from 10 sec to 25 min, even more preferably from 10 sec to 10 min, especially from 10 sec to 5 min, more especially from 10 sec to 1 min.

When REAC1 is done batch wise, then preferably compound of formula (1) is dissolved in a mixture of concentrated sulfuric acid and oleum to form a solution, and this solution is then mixed with the fuming nitric acid in order to provide for REAC1; more preferably the fuming nitric acid is added to said solution in order to provide for REAC1.

When REAC1 is done in a continuous way, then preferably compound of formula (1) is dissolved in a mixture of concentrated sulfuric acid and oleum forming a solution SOL1; this solution is then mixed continuously with a mixture MIX1 of concentrated sulfuric acid, oleum and fuming nitric acid in order to provide for REAC1.

Preferably, SOL1 contains
concentrated sulphuric acid in an amount of 2 to 10 times, more preferably of 2 to 7.5 times, even more preferably of 3.5 to 5 times, of molar equivalents of $H_2SO_4$ relative to compound of formula (1),
oleum in an amount of 1 to 10 times, more preferably of 1.2 to 6 times, even more preferably of 1.8 to 3.6 times, of molar equivalents of $H_2SO_4$ relative to compound of formula (1).

Preferably, MIX1 contains
concentrated sulphuric acid in an amount of 0.5 to 10 times, more preferably of 0.5 to 5 times, even more preferably of 0.5 to 2.5 times, especially of 0.5 to 1 times, of molar equivalents of $H_2SO_4$ relative to compound of formula (1),
oleum in an amount of 0.1 to 10 times, more preferably of 0.1 to 5 times, even more preferably of 0.1 to 2 times, especially of 0.1 to 1 times, more especially of 0.2 to 0.4 times, of molar equivalents of $H_2SO_4$ relative to compound of formula (1),
fuming nitric acid in an amount of 1.0 to 5 times, more preferably of 1.2 to 3.5 times, even more preferably of 1.5 to 2 times, of molar equivalents of $HNO_3$ relative to compound of formula (1).

When REAC1 is done in a continuous way, then preferably REAC1 is done in a mixing device MIXDEV, where a feed FEED1 containing compound of formula (1) is mixed with a feed FEED2 containing the fuming nitric acid, the mixing results is a reaction mixture. Preferably, FEED1 is SOL1 and FEED2 is MIX1.

MIXDEV can be any suitable installation which an be used for mixing two fluids and which is known in the state of the art, such as a common branch connection, e.g. a T or Y piece, a static mixing device or a micro reactor, preferably it is a static mixing device or a micro reactor.

Static mixing devices, e.g. static mixers, are well established and widespread in all fields of chemical process technology. It is characteristically for static mixing devices, that, in contrast to dynamic mixing devices, only the media to be mixed are in motion. The liquids or gases are mixed by pump energy only, while the geometrically strong defined mixing elements in the static mixing devices remain in position. Companies such as Fluitec, Seuzachstrasse, 8413 Neftenbach, Switzerland, or Sulzer Ltd, Neuwiesenstrasse 15, 8401 Winterthur, Switzerland, are well known suppliers among others of such static mixing devices.

Micro reactors, also called micro structured reactors, are devices in which chemical reactions take place in a confinement with typical lateral dimensions below 1 mm; the most typical form of such confinement are micro channels. A micro reactor is a continuous flow reactor. They have been successfully applied in lab, pilot and production scale. E.g. the Fraunhofer Institute for Chemical Technology ICT, Joseph-von-Fraunhofer Strasse 7, 76327 Pfinztal, Germany, develops and offers such micro reactors.

Preferably, the static mixing device has the form of a tube or a plate containing means that present obstacles for the flow of the reaction mixture and thereby effecting the mixing of the components.

Preferably, the micro reactor contains micro channels which are arranged in such a way as to effect the mixing.

After REAC1, compound of formula (2) can be isolated and purified by conventional methods, which are known to those skilled in the art. These conventional methods include quenching the reaction mixture from REAC1 with water, extraction, distillation, preferably fractional distillation, which can be done under reduced pressure, crystallization, chromatography, filtration, washing or any combination of these methods.

Further subject of the invention is a method for the preparation of compound of formula (6)

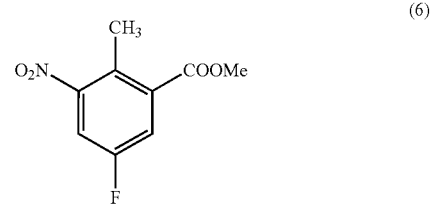

(6)

comprising the STEP1 and a second step STEP2;
STEP2 comprises a reaction REAC2, in REAC2 compound of formula (2), which is obtained by REAC1 in STEP1, is reacted with methanol to provide compound of formula (6);

with STEP1 as defined above, also with all its embodiments.

Preferably, the molar amount of methanol in REAC2 is from 1 to 50 times, more preferably from 5 to 20 times, even more preferably from 7.5 to 15 times, of the molar amount of compound of formula (2).

Preferably, REAC2 is done in the presence of an acid ACID2, ACID2 is preferably $H_2SO_4$.

Preferably, the molar amount of ACID2 is from 1 to 50 times, preferably 1 to 40 times, more preferably 1 to 30 times, more preferably 5 to 20 times, of the molar amount of compound of formula (2).

REAC2 can be done batch wise or in a continuous way. Preferably, the reaction temperature TEMP2 of REAC2 is from 80 to 120° C., more preferably from 90 to 110° C. The reaction time TIME2 of REAC2 is preferably from 10 sec to 24 h, more preferably from 1 min to 12 h.

When REAC2 is done batch wise, then
preferably, the reaction time TIME2 of REAC2 is from 30 min to 24 h, more preferably from 1 h min to 12 h.
When REAC2 is done in a continuous way, then
preferably, the reaction time TIME2 of REAC2 is from 10 sec to 30 min, more preferably from 1 min to 15 min.

Preferably, both REAC1 and REAC2 are done in a continuous way and are preferably done consecutively without isolation of compound of formula (2), preferably the reaction mixture from REAC1 is used as the substrate feed for REAC2, preferably without interruption of the flow of the feeds.

After REAC2, compound of formula (6) can be isolated and purified by conventional methods, which are known to those skilled in the art. These conventional methods include quenching the reaction mixture from REAC2 with water, extraction, distillation, preferably fractional distillation, which can be done under reduced pressure, crystallization, chromatography, filtration, washing or any combination of these methods.

EXAMPLES

HPLC Procedure
Column: Phenomenex Kinetex C-18 100×4.6 mm, 2.6 micrometer
Temperature: 25° C.
Solvent A: Acetonitrile
Solvent B: 0.05% (v/v) aqueous TFA
Flow: 1.3 mL/min
Gradient (v/v):
within 30 min: Solvent A:Solvent B from 5%:95% to 95%:5%
within 1 min: Solvent A:Solvent B from 95%:5% to 5%:95%
for 4 min: Solvent A:Solvent B 5%:95%

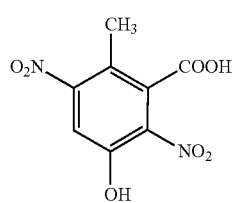
(4)

dinitro derivative, the compound of formula (4)

Comparative Example 1—With Concentrated Sulphuric Acid and With Aqueous Nitric Acid of 65 wt %

10.0 g (0.065 mol, 1 eq) of compound of formula (1) were dissolved in 67.4 g of concentrated sulphuric acid (0.688 mol, 10.6 eq). The solution was cooled to 0° C. and 7.5 g of nitric acid (65 wt % aqueous solution, 0.078 mol, 1.2 eq) were added. After stirring for 1 h at 0° C., an HPLC chromatogram showed 80% conversion and 45% of the dinitro derivative, the compound of formula (4).

Comparative Example 2—With Concentrated Sulphuric Acid and With Fuming Nitric Acid 10.0 g (0.065 mol, 1 eq) of compound of formula (1) were dissolved in 67.4 g of concentrated sulphuric acid (0.688 mol, 10.6 eq). The solution was cooled to 0° C. and 5.0 g of fuming nitric acid (99 wt %, 0.078 mol, 1.2 eq) were added. After stirring for 1 h at 0° C., an HPLC chromatogram showed 80% conversion and 42% of the dinitro derivative, the compound of formula (4).

Example 1—With Oleum and With Fuming Nitric Acid 10.0 g (0.065 mol, 1 eq) of compound of formula (1) were dissolved in 67.4 g of concentrated sulphuric acid (0.688 mol, 10.6 eq, 96 to 100 wt %) and in 9.6 g of oleum (65% of $SO_3$, 0.078 mol, 1.2 eq). The solution was cooled to 0° C. and 5 g of fuming nitric acid (99 wt %, 0.078 mol, 1.2 eq) were added. After stirring for 1 h at 0° C., an HPLC chromatogram showed full conversion and less than 0.5% of the dinitro derivative, the compound of formula (4).

Example 2—Continuous Flow Nitration With Oleum and With Fuming Nitric Acid Followed by Esterification Step Nitration
Two feeds were prepared for the continuous flow nitration, a Feed 1 and a Feed 2:
Feed 1: 125 g of fuming nitric acid (99 wt %, 1.98 mol), 94.54 g of concentrated sulphuric acid (0.90 mol, 96 to 100 wt %) and 31.46 g of oleum (0.32 mol)
Feed 2: 177.55 g of compound of formula (1) (1.12 mol), 522.45 g of concentrated sulphuric acid (5.06 mol, 96 to 100 wt %) and 300 g of oleum (3.05 mol)
Feed 1 and Feed 2 were pumped using a separate pump for each feed. Feed 1 was pumped with 9.139 g/min, Feed 2 was pumped with 55.861 g/min.

The two feeds were initially pre-cooled to 20° C. using two plates, a plate with an internal volume of 19.5 mL for Feed 1 and a plate with an internal volume of 25.77 mL for Feed 2. After said cooling to 20° C., the feeds were mixed in the reactor, which was a FlowPlate® A5 mikroreactor, process plate LL, Ehrfeld Mikrotechnik BTS GmbH, D-55234 Wendelsheim, Germany, with a volume of 10.28 mL, at 20° C. and with a residence time of 17 sec. The crude product solution of compound of formula (2) exiting the reactor constituted the third feed, the Feed 3. An HPLC chromatogram of a sample of Feed 3 showed full conversion and less than 0.5% of the dinitro derivative, the compound of formula (4). After 60 min, the system was purged with dichloromethane. Feed 3 was used directly in the next step, the esterification.

Step Esterification

Feed 3 was pumped with 9.834 g/min and a fourth feed, the Feed 4, which was methanol, was pumped with a flow rate of 8.792 g/min (11 eq).

Initially, the two feeds were pre-heated to 100° C. using two plates, a plate with an internal volume of 5.13 mL for Feed 3 and a plate with an internal volume of 11.97 mL for Feed 4. After said heating to 100° C., the feeds were mixed in the reactor, which was a FlowPlate® A5 mikroreactor, process plate LL, Ehrfeld Mikrotechnik BTS GmbH, D-55234 Wendelsheim, Germany, with a volume of 2.05 mL, at 100° C., the residence time was 6 min. The reaction solution exiting the reactor was then passed through a coil heated at 100° C. providing for a residence time of 6 min. An HPLC chromatogram of a sample of the crude product solution of compound of formula (6) exiting the coil showed full conversion and less than 0.5% of the starting material, the compound of formula (2). After 20 min, the system was purged with methanol. The crude product solution was cooled to 20° C. whereby compound of formula (6) precipitated, the solid was isolated by filtration and dried under vacuum (40° C., 20 mbar, 10 h). 221 g of compound of formula (6) were obtained as a colorless solid (yield: 90%, purity: 99.2%).

The invention claimed is:

1. A method for the preparation of a compound of formula (2)

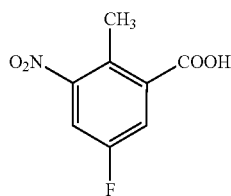

(2)

comprising a step STEP1, wherein STEP1 comprises a reaction REAC1, wherein in REAC1 a compound of formula (1)

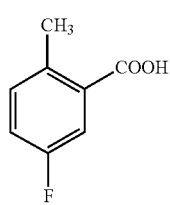

(1)

is converted to the compound of formula (2) by the action of a mixture MIX of concentrated sulphuric acid, oleum and fuming nitric acid.

2. The method according to claim 1, wherein
the concentrated sulfuric acid has a content of from 94 to 100 wt % of $H_2SO_4$; the wt % based on the weight of the concentrated sulfuric acid.

3. The method according to claim 1, wherein
the oleum contains 50 to 70 wt % of $SO_3$.

4. The method according to claim 1, wherein
the fuming nitric acid has a content of from 95 to 100 wt % of $HNO_3$.

5. The method according to claim 1, wherein
MIX comprises:
concentrated sulphuric acid in an amount of 4 to 12 times of molar equivalents of $H_2SO_4$ relative to compound of formula (1),
oleum in an amount of 1 to 4 times of molar equivalents of $H_2SO_4$ relative to compound of formula (1), and
fuming nitric acid in an amount of 1 to 2 times of molar equivalents of $HNO_3$ relative to compound of formula (1).

6. The method according to claim 1, wherein
the amounts of concentrated sulfuric acid, oleum and fuming nitric acid in MIX add up to 95 to 100 wt % based on the total weight of MIX.

7. The method according to claim 1, wherein
the reaction temperature TEMP1 of REAC1 is from −10 to 30° C.

8. The method according to claim 1, wherein
the reaction time TIME1 of REAC1 is from 1 sec to 2 h.

9. The method according to claim 1, wherein
REAC1 is done in a continuous way.

10. A method for the preparation of a compound of formula (6)

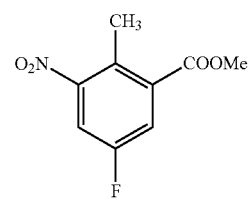

(6)

comprising the STEP1 and a second step STEP2;
wherein STEP2 comprises a reaction REAC2, wherein in REAC2 the compound of formula (2), which is obtained by REAC1 in STEP1, is reacted with methanol to provide the compound of formula (6);
with STEP1 as defined in claim 1.

11. The method according to claim 10, wherein
REAC2 is done in the presence of an acid ACID2, wherein ACID2 is $H_2SO_4$.

12. The method according to claim 10, wherein
both REAC1 and REAC2 are done in a continuous way and are done consecutively without isolation of compound of formula (2).

13. The method according to claim 1, wherein
the amounts of concentrated sulfuric acid, oleum and fuming nitric acid in MIX add up to 98 to 100 wt %, based on the total weight of MIX.

14. The method according to claim 1, wherein MIX consists of concentrated sulfuric acid, oleum and fuming nitric acid.

* * * * *